United States Patent
Stinson et al.

(10) Patent No.: US 6,620,122 B2
(45) Date of Patent: Sep. 16, 2003

(54) GASTRIC PSEUDOCYST DRAINAGE AND STENT DELIVERY SYSTEM FOR USE THEREIN

(75) Inventors: Jonathan S. Stinson, Plymouth, MN (US); M. Kevin Richardson, Hopkinton, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/843,449

(22) Filed: Apr. 26, 2001

(65) Prior Publication Data

US 2002/0161341 A1 Oct. 31, 2002

(51) Int. Cl.⁷ .................................. A61M 5/00
(52) U.S. Cl. ........................ 604/8; 604/96.01
(58) Field of Search .................. 604/8, 93.01, 264, 604/540, 541, 542, 543, 544; 623/23.7; 606/108

(56) References Cited

U.S. PATENT DOCUMENTS

| | | | |
|---|---|---|---|
| 4,733,665 A | | 3/1988 | Palmaz |
| 4,922,905 A | | 5/1990 | Strecker |
| 4,950,227 A | | 8/1990 | Savin et al. |
| 5,591,172 A | * | 1/1997 | Bachmann et al. ......... 623/1.11 |
| 5,674,276 A | * | 10/1997 | Andersen et al. ............ 623/1.5 |
| 6,015,431 A | * | 1/2000 | Thornton et al. ........... 606/194 |

OTHER PUBLICATIONS

Dean et al., "Pancreatic pseudocyst with gastric and colonic connections treated conservatively," Br. J. Surg., 67:429–30 (1980).

Libera et al., "Pancreatic Pseudocysts Transpapillary and Transmural Drainage, " HPB Surgery, 11:333–8 (2000).

Vitale et al., "Endoscopic drainage of the pancreatic pseudocyst," Surgery, 126 (4) :616–23 (1999).

Espinel et al., Endoscopic Transpapillary Drainage of an Infected Pancreatic Fluid Collection in Pancreas Divisum, Digestive Diseases and Sciences, 45(2):237–41 (2000).

Pages 39–50 of Wound Closure Biomaterials and Devices, edited by Chih–Chang Chu, J. Anthony Fraunhofer and Howard P. Greisler, published by CRC Press, Inc. (1997).

Davies et al., "Percutaneous Cystogastrostomy with a New Catheter for Drainage of Pancreatic Pseudocysts and Fluid Collections,"Cardiovasc. Intervent. Radiol., 19:128–31 (1996).

Milici et al., "Gastric Intramural Pseudocyst: Computed Tomographic Diagnosis," Gastrointest. Radiol., 14:113–4 (1989).

\* cited by examiner

Primary Examiner—Edward K. Look
Assistant Examiner—John K Fristoe, Jr.
(74) Attorney, Agent, or Firm—Kriegsman & Kriegsman (57) ABSTRACT

Method for draining pseudocysts and stent delivery system for use therein. In one embodiment, the system comprises an inner catheter provided with a pair of longitudinal lumens. A guide wire is slidably disposed in one lumen, and a retractable needle is slidably disposed in the other lumen. A self-expandable stent is coaxially mounted around the inner catheter near its distal end, and an outer catheter is coaxially mounted around the inner catheter and the stent, the outer catheter being adapted for axial movement relative to the inner catheter and being dimensioned to maintain the stent in a compressed state. In use, an endoscope is intraorally introduced into a patient's stomach, and the distal end of the system is inserted therethrough. The needle is advanced to form perforations in the stomach and pseudocyst. The inner catheter is then inserted through the perforations, and the outer catheter is retracted, allowing the stent to expand and interconnect the stomach and pseudocyst. The endoscope and the rest of the delivery system are then withdrawn from the patient.

27 Claims, 7 Drawing Sheets

GASTRIC PSEUDOCYST DRAINAGE AND STENT DELIVERY SYSTEM FOR USE THEREIN

BACKGROUND OF THE INVENTION

The present invention relates generally to gastric pseudocyst drainage and relates more particularly to a novel method for draining gastric pseudocysts and to a novel stent delivery system for use in said method.

A gastric or pancreatic pseudocyst is an aggregation of tissue, fluid, debris, pancreatic enzymes and blood that often develops in the peritoneal cavity after the onset of acute pancreatitis. Although many pseudocysts resolve themselves spontaneously, some pseudocysts become quite large and require treatment due to the unwanted pressure they exert against the stomach and/or neighboring organs.

One approach to treating gastric pseudocysts involves surgery and typically comprises (i) cutting through the abdominal wall of the patient to permit access to the pseudocyst through the abdominal wall, (ii) perforating or puncturing the pseudocyst, (iii) inserting a drainage tube into the pseudocyst through the perforation to allow the contents of the pseudocyst to empty through the drainage tube to a point external to the patient, (iv) removing the drainage tube from the patient once the pseudocyst has been emptied, and (v) repairing the abdominal wall.

As can readily be appreciated, the surgical approach described above is invasive and has easily identifiable drawbacks associated therewith, such as an appreciable risk of infection.

More recently, an endoscopic approach to treating gastric pseudocysts has been devised. This approach is less invasive than surgery and typically involves inserting an endoscope through the patient's mouth and into the patient's stomach. The endoscope is first used to visually locate the pseudocyst on the opposite side of the stomach wall. A needle or sphincterotome is then extended through the distal end of the endoscope to perforate both the stomach wall and the pseudocyst. A contrast agent delivered through the endoscope is then injected into the pseudocyst, and a cystogram is endoscopically performed to confirm entry into a pseudocyst (as opposed to entry into the peritoneal cavity). Following confirmation of entry into a pseudocyst, a guide wire is advanced through the endoscope and into the pseudocyst. Next, a balloon catheter is advanced through the endoscope and over the guide wire into the pseudocyst. The balloon is dilated to enlarge the perforations in the pseudocyst and the stomach and is then deflated and withdrawn. A plurality of straight endobiliary tubes of fixed diameter (each approximately 10 Fr) are then endoscopically implanted across the pseudocyst and stomach perforations to allow the contents of the pseudocyst to drain into the stomach, said biliary tubes being arranged in a side-by-side fashion and being implanted one at a time. The endoscope is then removed from the patient. When drainage is complete (typically within a few weeks), the endoscope is reintroduced into the patient, and the biliary tubes are withdrawn from the patient through the endoscope using a snare.

Although the aforementioned endoscopic approach has certain advantages over the surgical approach described above, the foregoing endoscopic approach still suffers from certain drawbacks. One such drawback is that the biliary tubes presently used are relatively small in diameter and have a tendency to become occluded during use. Such occlusion is due, in part, to the inward radial pressure exerted by the pseudocyst and stomach walls against the tubes, and is due, in part, to the viscous nature of the materials conveyed within the small diameter tubes. Another drawback is that the biliary tubes used are susceptible to dislodgement from the pseudocyst and/or the stomach because they are straight and lack anchoring means. Still another drawback is that a second endoscopic procedure is needed to remove the biliary tubes from the patient following drainage of the pseudocyst. Still yet another drawback is that a multitude of different catheters or other devices must be sequentially inserted into the endoscope to enable the various steps outlined above to be performed.

SUMMARY OF THE INVENTION

It is an object of the present invention to provide a novel technique for draining gastric pseudocysts.

It is another object of the present invention to provide a technique as described above that overcomes at least some of the above-described shortcomings associated with existing techniques for draining gastric pseudocysts.

Therefore, in furtherance of the above and other objects to be described or to become apparent from the description below, there is provided herein a method of draining a pseudocyst present within a patient, said method comprising, according to one aspect, the steps of (a) providing a stent, said stent being transformable from a non-expanded state of comparatively lesser diameter to an expanded state of comparatively greater diameter, said stent having a first end and a second end; (b) delivering said stent in said non-expanded state to a pseudocyst located within a patient; (c) inserting said first end of said stent into the pseudocyst; and (d) transforming said stent from said non-expanded state to said expanded state; (e) whereby the pseudocyst drains through said stent.

Preferably, the aforementioned method further comprises the steps of inserting said second end of said stent into the stomach of the patient whereby the pseudocyst drains through said stent into the stomach and, prior to said first end and second end inserting steps, forming a perforation in each of the pseudocyst and the stomach, wherein said first end inserting step comprises inserting said first end of said stent through said perforations in the pseudocyst and the stomach. Moreover, the stent is preferably introduced into the stomach of the patient intraorally.

The above-described stent may be a self-expandable stent or may be a balloon-expandable stent. In the case of a self-expandable stent, said delivering step comprises maintaining said stent in said non-expanded state using a removable restraint, and said transforming step comprises removing said removable restraint from said stent to allow said stent to self-expand. The self-expandable stent, which is preferably made of a braided filamentary material, may be shaped to include a waist of comparatively lesser expanded diameter (e.g., 8–10 mm) and a pair of cuffs on opposite ends of said waist of comparatively greater expanded diameter (e.g., about 15 mm) or may have a uniform relaxed diameter. The self-expandable stent may be made of a biocompatible nonabsorbable material, such as a metal or a plastic, or may be made of a bioabsorbable material.

Where the stent is a balloon-expandable stent, said balloon-expandable stent is preferably a covered balloon-expandable stent. In addition, said delivering step preferably comprises mounting said balloon-expandable stent, in said non-expanded state, over a deflated balloon catheter and then inserting said deflated balloon catheter into a patient in the area of a pseudocyst. Said transforming step preferably comprises inflating said deflated balloon catheter until said balloon-expandable stent is transformed from said non-expanded state to said expanded state.

Where the stent, whether self-expandable or balloon-expandable, is nonabsorbable, the method preferably further comprises the step of endoscopically removing said stent with a snare after drainage of the pseudocyst is complete.

According to another aspect of the invention, there is provided a method of draining a pseudocyst present within a patient, said method comprising the steps of (a) providing a double pigtail stent, said double pigtail stent having a first end and a second end, each of said first and second ends being transformable from a straightened state, when constrained, to a curled state, when relaxed; (b) coaxially mounting said double pigtail stent over the distal end of a catheter, whereby each of said first and second ends is in said straightened state; (c) endoscopically introducing said double pigtail stent and the distal end of said catheter through the mouth and into the stomach of a patient in the vicinity of a pseudocyst; (d) sliding said first end of said double pigtail stent off the distal end of said catheter, through the stomach and into the pseudocyst, whereby said first end is transformed from said straightened state to said curled state; and (e) sliding said second end of said double pigtail stent off the distal end of said catheter into the stomach, whereby said second end is transformed from said straightened state to said curled state; (f) whereby the pseudocyst drains through said stent into the stomach.

Preferably, the aforementioned method further comprises, after said endoscopic introducing step and before said sliding steps, the step of forming a perforation in each of the stomach and the pseudocyst, said first end sliding step comprising sliding said first end of said double pigtail stent off the distal end of said catheter and through the perforations in the stomach and pseudocyst, respectively. In addition, the distal end of said catheter preferably includes a balloon, said method further comprising, after said perforation forming step and before said sliding steps, the steps of inserting said balloon into said perforations, then inflating said balloon, then deflating said balloon and withdrawing said balloon from said perforations. After drainage of the pseudocyst is complete, the foregoing double pigtail stent is preferably endoscopically removed using a snare.

The present invention is also directed to a stent delivery system, said stent delivery system comprising, in a first embodiment, (a) an inner catheter, said inner catheter being provided with a first longitudinally extending lumen; (b) perforating means slidably disposed in said first longitudinally extending lumen; (c) an outer catheter, said outer catheter surrounding at least a portion of the length of said inner catheter and adapted for axial movement relative to said inner catheter; and (d) a self-expandable stent, said self-expandable stent disposed between said inner catheter and said outer catheter; (e) wherein said outer catheter is dimensioned to maintain said self-expandable stent in a compressed state.

Preferably, the aforementioned self-expandable stent is coaxially mounted over said inner catheter, said self-expandable stent being made of braided filamentary material. Said self-expandable stent may be made of nonabsorbable material or may be made of bioabsorbable material. Said self-expandable stent may be shaped to have a uniform relaxed diameter or may be shaped to include a waist of comparatively lesser expanded diameter and a pair of cuffs on opposite ends of said waist of comparatively greater expanded diameter.

The perforating means of the subject stent delivery system preferably comprises a retractable needle. The inner catheter of said stent delivery system is preferably provided with a second longitudinal lumen, a guide wire being slidably disposed in said second longitudinal lumen.

In a second embodiment, the stent delivery system of the present invention comprises (a) a catheter, said catheter having a proximal end, a distal end, a first lumen extending longitudinally through said distal end and a second lumen extending longitudinally and having a proximal end connected to a gas line and a distal end terminating in a balloon section; (b) perforating means slidably disposed in said first lumen; and (c) a balloon-expandable stent coaxially mounted over said balloon section of said catheter.

Preferably, the aforementioned balloon-expandable stent is a balloon-expandable covered stent. In addition, the above-described stent delivery system preferably further comprises a sheath, said sheath surrounding at least a portion of the length of said catheter and said balloon-expandable stent and being adapted for axial movement relative to said catheter. Said catheter preferably further comprises third and fourth lumens extending longitudinally through said distal end, said third lumen receiving a slidably mounted guide wire, said fourth lumen being connected at its proximal end to a line containing dye for use in performing a cystogram.

In a third embodiment, the stent delivery system of the present invention comprises a stent delivery system comprising (a) a catheter, said catheter having a proximal end, a distal end, a first lumen extending longitudinally through said distal end, and a second lumen extending longitudinally and having a proximal end connected to a gas line and a distal end terminating in a balloon section; (b) perforating means slidably disposed in said first lumen; and (c) a first pigtail stent coaxially and slidably mounted over said catheter proximal to said balloon section.

Preferably, the aforementioned stent delivery system further comprises a pusher sleeve coaxially and slidably mounted over said catheter proximal to said first pigtail stent for pushing said first pigtail stent off said distal end of said catheter. In addition, said stent delivery system preferably further comprises a second pigtail stent coaxially and slidably mounted over said catheter proximal to said balloon section and distal to said first pigtail stent. Said catheter preferably further comprises third and fourth lumens extending longitudinally through said distal end, said third lumen receiving a slidably mounted guide wire, said fourth lumen being connected at its proximal end to a line containing dye for use in performing a cystogram.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
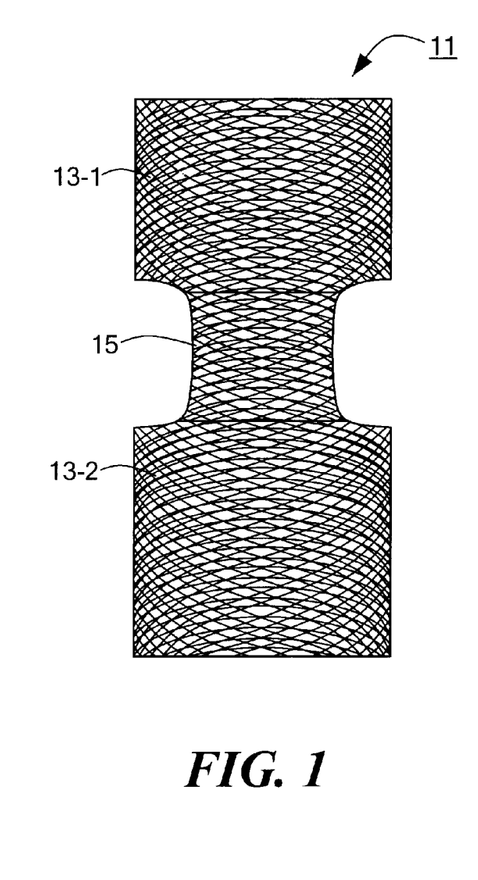
FIG. 1 is a side view of a first embodiment of a stent adapted for use in draining a gastric pseudocyst in accordance with the teachings of the present invention.

Referring now to FIG. 1, there is shown a side view of a first embodiment of a stent adapted for use in draining a gastric pseudocyst in accordance with the teachings of the present invention, said stent being represented generally by reference numeral 11.

Stent 11 is a self-expandable stent (i.e., tubular endoprosthesis) shaped to include a pair of cuffs 13-1 and 13-2 of comparatively large relaxed diameter (i.e., approximately 15 mm) and a midsection or waist 15 of comparatively small relaxed diameter (i.e., approximately 8–10 mm). As will be seen below, waist 15 is adapted to be inserted through the perforations formed in a stomach and a pseudocyst, and cuffs 13-1 and 13-2 are adapted to engage the walls of the stomach and the pseudocyst, respectively, in order to prevent the longitudinal displacement of stent 11 relative thereto. Each of cuffs 13-1 and 13-2 and waist 15 has a length of approximately 5–10 mm.

Although, in the present embodiment, stent 11 is made by braiding filamentary material, it can readily be appreciated that stent 11 could alternatively be made, for example, by coiling, crocheting or knitting filamentary material or by any other suitable manufacturing process. Braiding may be preferred, however, since it is a comparatively inexpensive manufacturing technique that results in a structurally sound product from an engineering standpoint. The filamentary material used to make stent 11 is nonabsorbable and may be a metal filament, such as a nitinol (a nickel/titanium alloy) wire, or may be a nonabsorbable polymeric filament. A nonabsorbable polymeric filament may be preferred over a metal filament since stents made of metal wire often possess sharp ends, which may be injurious to a stomach wall. As can readily be appreciated, one can modify the radial self-expansion force exerted by stent 11 by correspondingly modifying the thickness of the filament used to make stent 11 (i.e., the thicker the filament, the greater the radial self-expansion force).

Stent 11 may be coated with an antibiotic to prevent infection; alternatively, an antibiotic may be incorporated into the filamentary material used to make stent 11.

Figure 2:
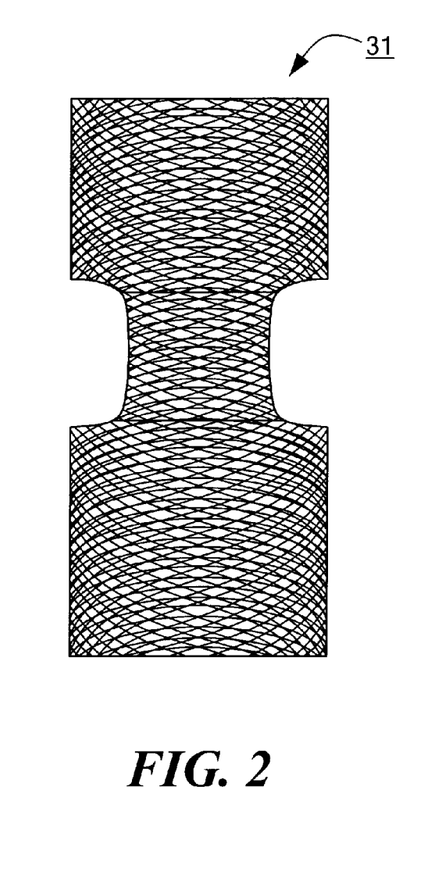
FIG. 2 is a side view of a second embodiment of a stent adapted for use in draining a gastric pseudocyst in accordance with the teachings of the present invention.

Referring now to FIG. 2, there is shown a side view of a second embodiment of a stent adapted for use in draining a gastric pseudocyst in accordance with the teachings of the present invention, said stent being represented generally by reference numeral 31.

Stent 31 is similar in most respects to stent 11, the only difference between the two stents being that stent 31 is made from one or more bioabsorbable materials including, but not limited to, homopolymers and copolymers of glycolide, lactide, ε-caprolactone and p-dioxanone, copolymers of glycolide and trimethylene carbonate, as well as polyanhydrides and polyorthoesters. Additional examples of bioabsorbable materials that may be used to make stent 31 are disclosed in pages 39–50 of *Wound Closure Biomaterials and Devices*, edited by Chih-Chang Chu, J. Anthony von Fraunhofer and Howard P. Greisler, published by CRC Press, Inc. (1997), which is incorporated herein by reference.

As can readily be appreciated, one can alter the life span of stent 31 as desired by modifying the type of bioabsorbable material used in stent 31 and/or by modifying the thickness of the filamentary material used to make stent 31. Preferably, stent 31 has a life span on the order of about 3–6 weeks, which is generally the maximum amount of time needed for a gastric pseudocyst to drain.

Figure 3:
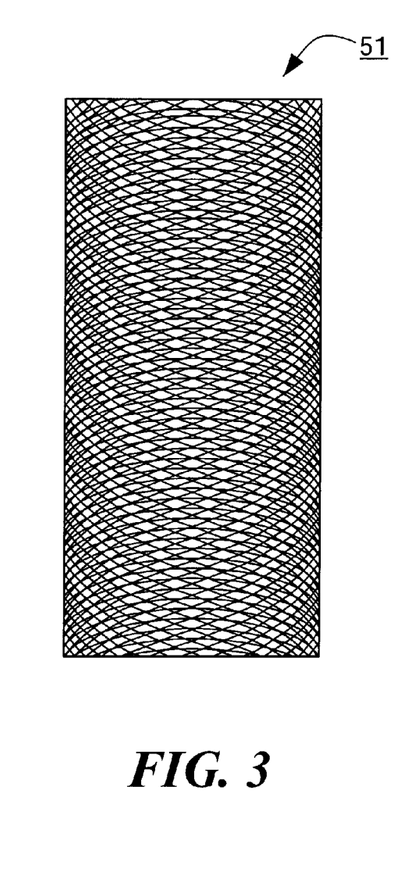
FIG. 3 is a side view of a third embodiment of a stent adapted for use in draining a gastric pseudocyst in accordance with the teachings of the present invention.

Referring now to FIG. 3, there is shown a side view of a third embodiment of a stent adapted for use in draining a gastric pseudocyst in accordance with the teachings of the present invention, said stent being represented generally by reference numeral 51.

Stent 51 is similar in most respects to stent 11, the principal differences between the two stents being that stent 51 has a uniform diameter along its length and may be made of either a nonabsorbable material or a bioabsorable material. As can readily be appreciated, when stent 51 is implanted in a patient, the shape of stent 51 will tend to resemble that of stents 11 and 31 since the midsection of stent 51 will tend to be compressed by the stomach and pseudocyst walls whereas the ends of stent 51 will tend to be less compressed and, therefore, more free to expand to their relaxed states.

Figure 4:
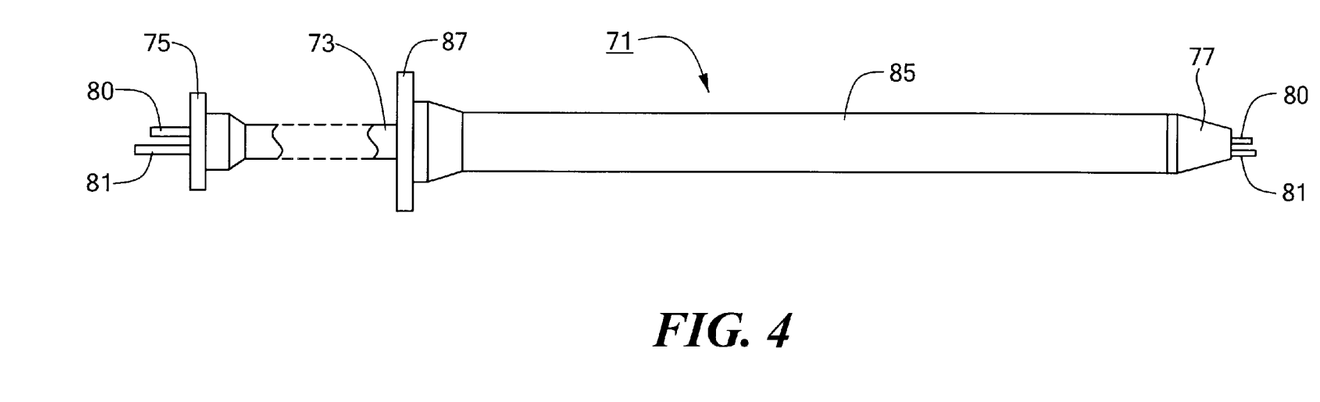
FIG. 4 is a side view of a first embodiment of a stent delivery system constructed according to the teachings of the present invention, said stent delivery system including the stent of FIG. 1.
Figure 5:
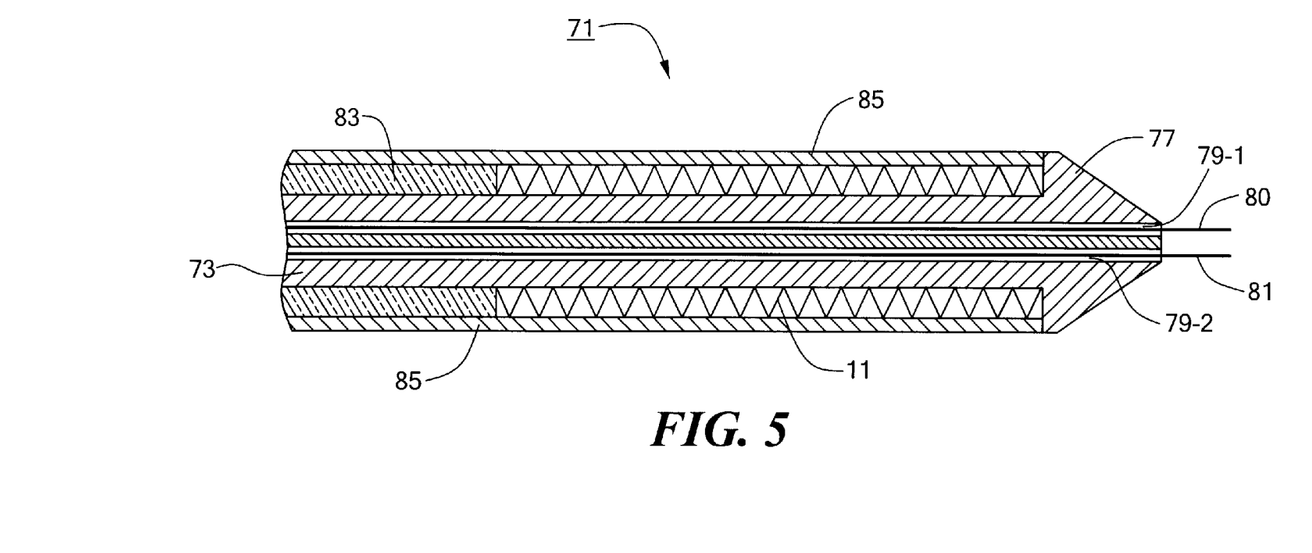
FIG. 5 is a fragmentary schematic longitudinal section view of the stent delivery system of FIG. 4, showing the distal end thereof.
Figure 6A:
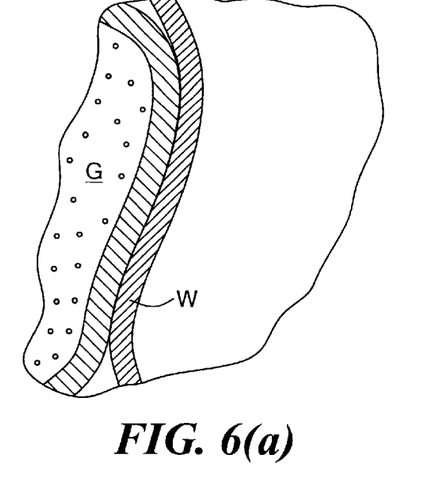
FIGS. 6(a) through 6(h) are fragmentary schematic views, partly in section, illustrating how the stent delivery system of FIG. 4 may be used endoscopically to perform the gastric drainage method of the present invention.
Figure 6B:
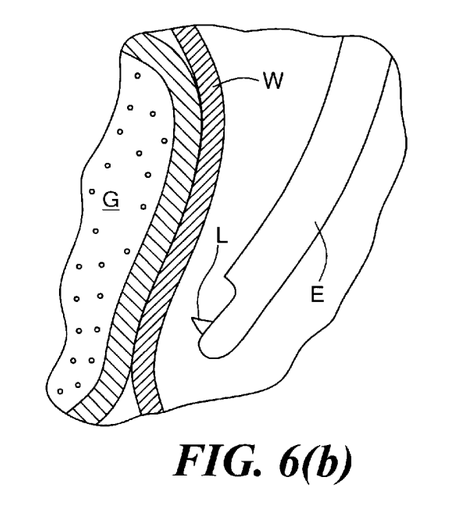
Figure 6C:
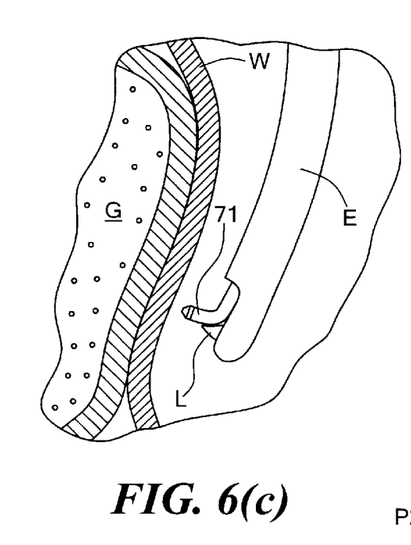
Figure 6D:
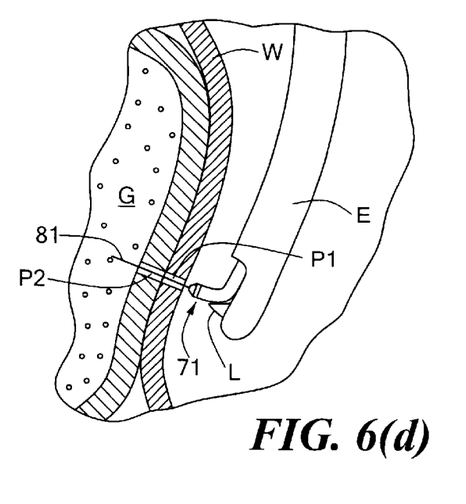
Figures 6E, 6F, 6G, 6H:
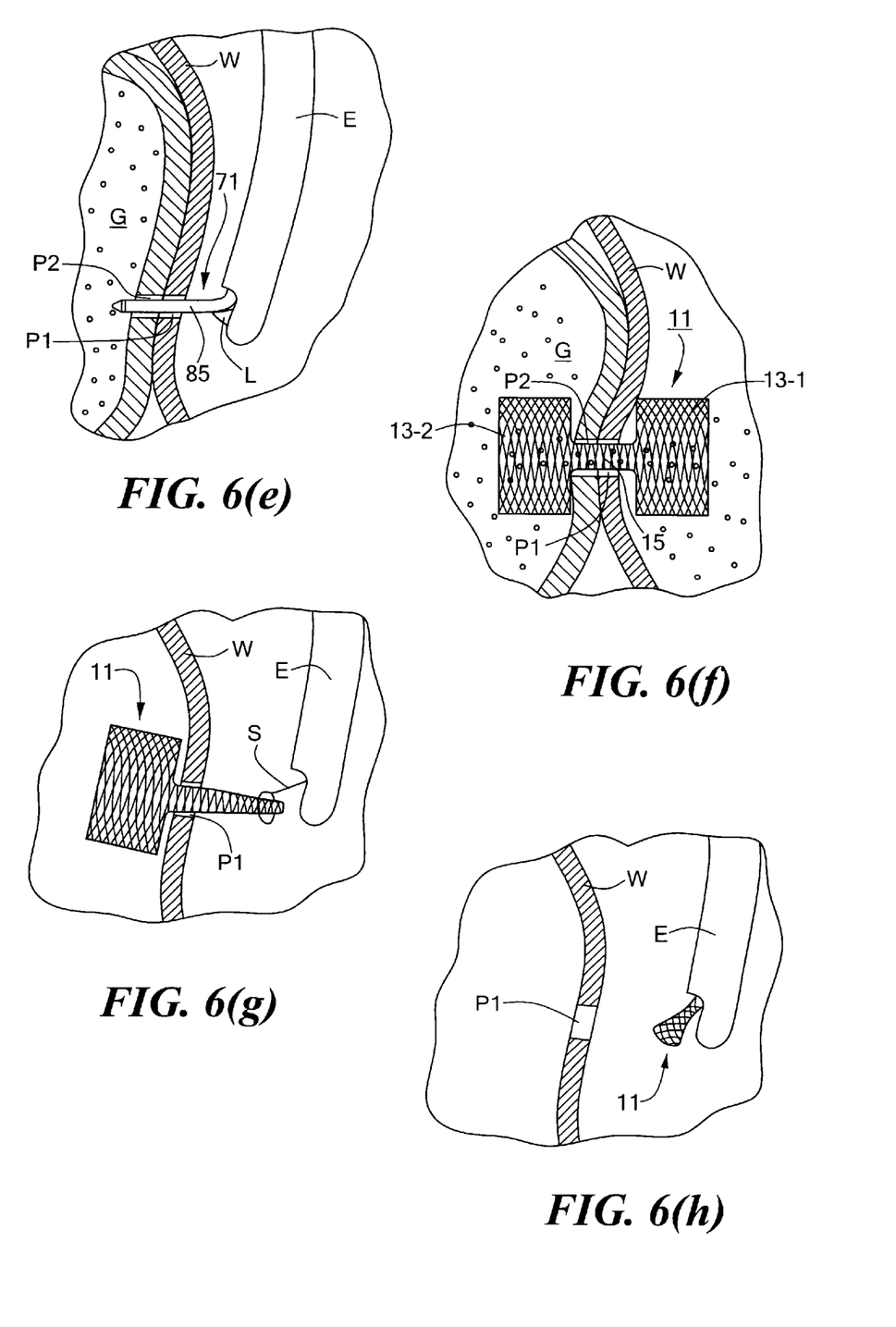

Referring now to FIGS. 4 and 5, there are shown side and fragmentary schematic longitudinal section views, respectively, of a first embodiment of a stent delivery system constructed according to the teachings of the present invention, said stent delivery system being represented generally by reference numeral 71.

System 71 comprises a flexible, inner catheter 73. A handle 75 is disposed at the proximal end of catheter 73, and an enlarged tip 77 is disposed at the distal end of catheter 73. A pair of parallel lumens 79-1 and 79-2 extend longitudinally through catheter 73. A guide wire 80 is removably received within lumen 79-1 and is adapted for use in positioning system 71 at a desired position within a body lumen. A retractable needle 81 is removably received within lumen 79-2 and is adapted for use in perforating the stomach and pseudocyst walls. (Needle 81 may be replaced with a retractable knife or with a retractable, electrically-conductive cauterizing device, such as a needle-knife sphincterotome.)

System 71 also comprises a self-expandable stent, said self-expandable stent being mounted over catheter 73 in a stretched or compressed state proximally relative to tip 77. Although, in the present embodiment, said self-expandable stent is stent 11, it can readily be appreciated that stent 11 may be replaced with stent 31, stent 51 or any other suitable self-expandable stent. A space-filling jacket 83 is secured (e.g., by a friction-fit) to catheter 73 proximally relative to stent 11. Jacket 83 serves to prevent proximal sliding of stent 11 during deployment.

System 71 further comprises a flexible, outer catheter 85. Catheter 85 coaxially surrounds much of the distal end of catheter 73 up to tip 77 and, additionally, coaxially surrounds and maintains stent 11 in its stretched or compressed state. Catheter 85 is adapted for axial movement relative to catheter 73, and a handle 87 is disposed at the proximal end of catheter 85 for use in axially moving catheter 85 relative to catheter 73.

Referring now to FIGS. 6(*a*) through 6(*h*), there is illustrated the manner in which system 71 may be used to drain a gastric pseudocyst. In FIG. 6(*a*), a gastric pseudocyst G is shown pressing inwardly against the exterior surface of a stomach wall W. In FIG. 6(*b*), the distal end of an endoscope E is inserted into the stomach (presumably through the mouth of the patient) and is positioned in the vicinity of where stomach wall W is contacted by pseudocyst G. In FIG. 6(*c*), the distal end of system 71 is advanced out through the distal end of endoscope E towards the distended portion of stomach wall W, the distal end of system 71 being deflected 90° relative to the longitudinal axis of endoscope E by an elevator L pivotally mounted on endoscope E at its distal end. In FIG. 6(*d*), needle 81 is advanced from the distal end of system 71 to form perforations P1 and P2 in stomach wall W and pseudocyst G, respectively. Needle 81 is then retracted. In FIG. 6(*e*), the distal end of system 71 is advanced into pseudocyst G through perforations P1 and P2. Outer catheter 85 of system 71 is then retracted proximally, thereby allowing stent 11 to self-expand. Inner catheter 73 and endoscope E are then retracted proximally, leaving stent 11 in place with cuffs 13-1 and 13-2 engaging pseudocyst G and the stomach wall W, respectively, and waist 15 extending therebetween through perforations P1 and P2. As shown in FIG. 6(*f*), with stent 11 in place, the contents of pseudocyst G are permitted to drain into the stomach. This may take up to about 3–6 weeks. As shown in FIGS. 6(*g*) and 6(*h*), when drainage is complete, endoscope E is reintroduced into the stomach (preferably via the mouth), and a snare S is advanced from the distal end of endoscope E to withdraw stent 11 from the patient.

It should be understood that the aforementioned procedure may also include an endoscopically-aided preliminary examination of the stomach and pseudocyst, as well as an endoscopically-aided cystogram of the type described above.

As can readily be appreciated, some of the advantages of using stent 11, as compared to conventional endobiliary tubes, to drain gastric pseudocysts are that (i) the expanded diameter of stent 11 is larger than the fixed diameter of an individual endobiliary tube (about 8–10 mm vs. about 3–5 mm, respectively), thereby resulting in faster drainage and obviating the need for a plurality of drainage members to be implanted; (ii) due to the anchoring action of cuffs 13-1 and 13-2, stent 11 is less likely to become longitudinally dislodged from a pseudocyst and/or stomach than are endobiliary tubes; and (iii) due to the radial expansion force exerted by stent 11, stent 11 is less likely to become constricted by radially inward forces exerted by a pseudocyst and/or stomach.

Bioabsorbable stent 31 has a further advantage over nonabsorbable stent 11 in that it does not require an additional endoscopic procedure for its removal since it degrades on its own within a few weeks after having been implanted in a patient. This is also advantageous for the reason that, within a few weeks after having been implanted in a patient, there is a tendency for stomach tissue to grow into a nonabsorbable stent, thereby making its removal from a patient more difficult and increasing the risk of injury to the patient.

Figure 7:
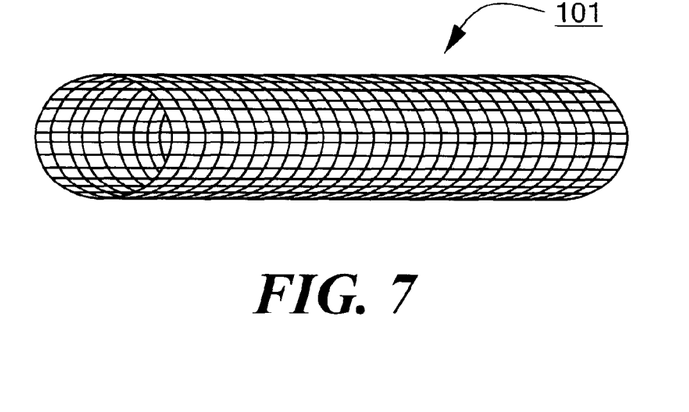
FIG. 7 is a perspective view of a fourth embodiment of a stent adapted for use in draining a gastric pseudocyst in accordance with the teachings of the present invention.

Referring now to FIG. 7, there is shown a perspective view of a fourth embodiment of a stent adapted for use in draining a gastric pseudocyst in accordance with the teachings of the present invention, said stent being represented generally by reference numeral 101.

Stent 101 is a balloon-expandable stent capable of being inelastically expanded to a diameter of about 8–10 mm. Examples of various balloon-expandable stents are disclosed in the following U.S. patents, all of which are incorporated herein by reference: U.S. Pat. No. 4,922,905, inventor Strecker, issued May 8, 1990; U.S. Pat. No. 4,950,227, inventors Savin et al., issued Aug. 21, 1990; and U.S. Pat. No. 4,733,665, inventor Palmaz, issued Mar. 29, 1988. Although in the present embodiment, stent 101 is a mesh tube made of a ductile metal, stent 101 is not limited in structure or materials thereto.

Figure 8A:
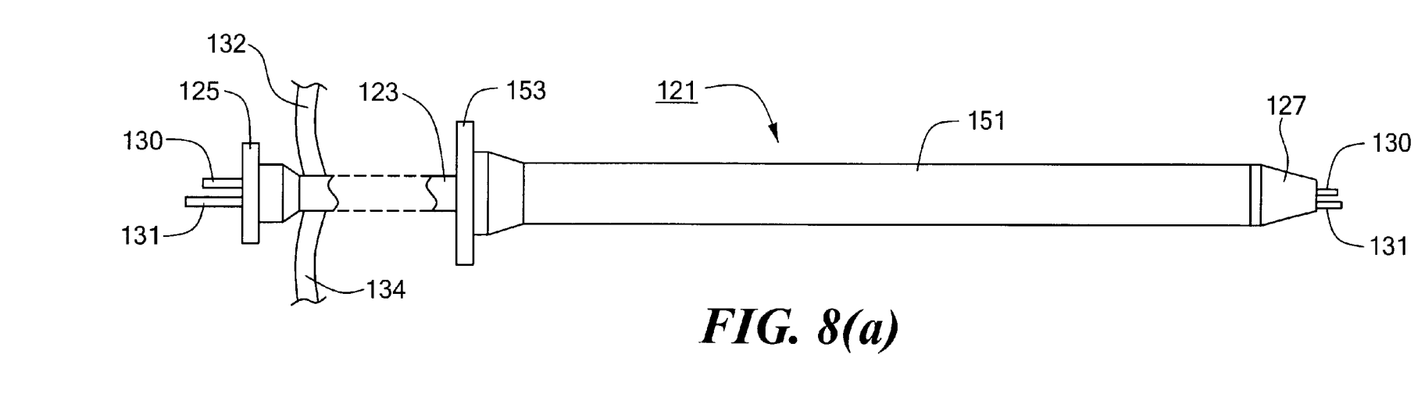
FIGS. 8(a) and 8(b) are fragmentary side and fragmentary schematic longitudinal section views, respectively, of a second embodiment of a stent delivery system constructed according to the teachings of the present invention, said stent delivery system including the stent of FIG. 7.
Figure 8B:
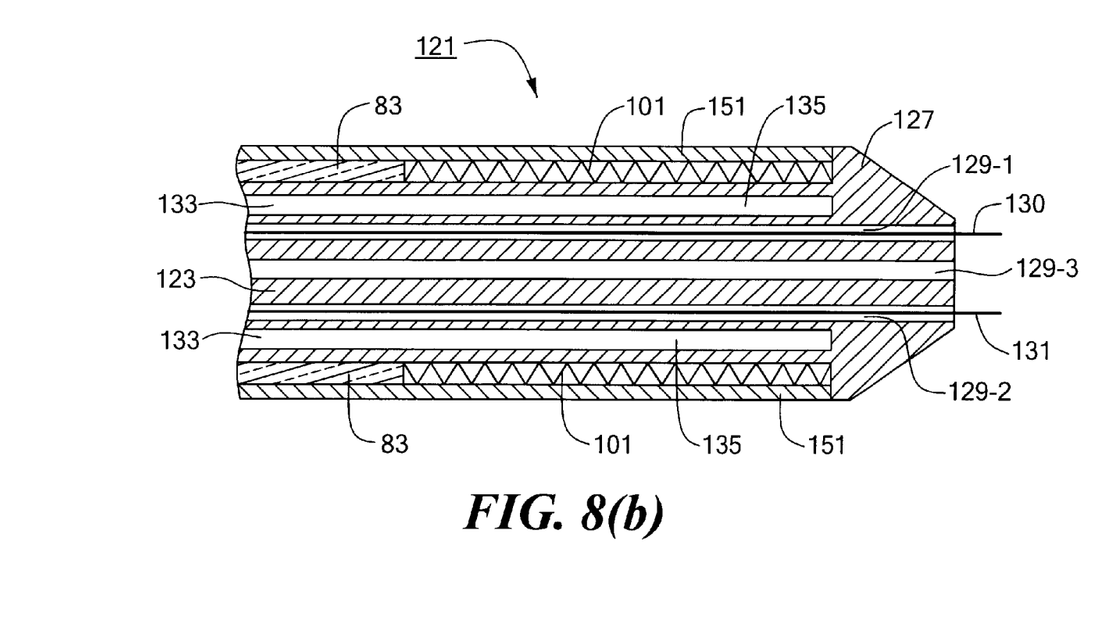

Referring now to FIGS. 8(*a*) and 8(*b*), there are shown fragmentary side and fragmentary schematic longitudinal section views, respectively, of a second embodiment of a stent delivery system constructed according to the teachings of the present invention, said stent delivery system being represented generally by reference numeral 121.

System 121 comprises a flexible catheter 123. A handle 125 is disposed at the proximal end of catheter 123, and a tip 127 is disposed at the distal end of catheter 123. A plurality of parallel lumens 129-1 through 129-3 extend longitudinally through catheter 123. A guide wire 130 is removably received within lumen 129-1 and is adapted for use in positioning system 121 at a desired position within a body lumen. A retractable needle 131 is removably received within lumen 129-2 and is adapted for use in perforating the stomach and pseudocyst walls. (Needle 131 may be replaced with a retractable knife, a retractable sphincterotome or the like.) Lumen 129-3 is coupled at its proximal end to a line 132 containing a dye of the type suitable for use in performing a cystogram of the pseudocyst. A fourth lumen 133, which is connected at its proximal end to a gas line 134, surrounds the distal ends of lumens 129-1 through 129-3 and ends in a balloon section 135 proximal to tip 127.

Figure 9:
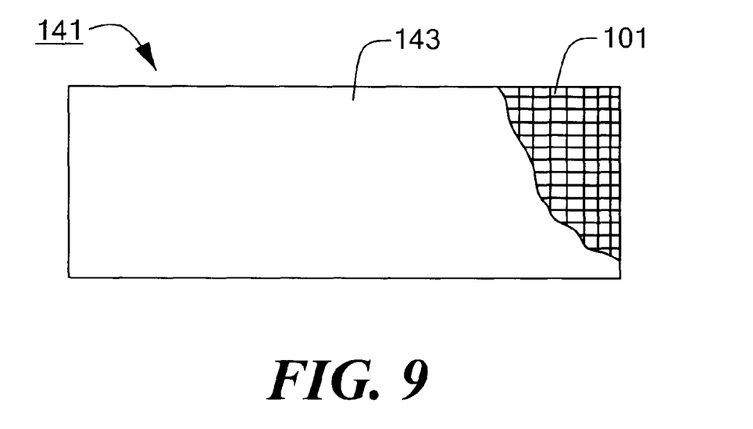
FIG. 9 is a side view, broken away in part, of a fifth embodiment of a stent adapted for use in draining a gastric pseudocyst in accordance with the teachings of the present invention.

System 121 also comprises a balloon-expandable stent, said balloon-expandable stent being coaxially arranged over balloon section 135. Although in the present embodiment, said balloon-expandable stent is stent 101, it can readily be appreciated that other balloon-expandable stents may also be suitable. (For example, stent 101 may be replaced with the fabric covered balloon-expandable stent 141 of FIG. 9. In fact, stent 141 may be preferred to stent 101 for gastric pseudocyst drainage for the reason that tissue growth into stent 141 is made more difficult by the presence of cover 143. Consequently, removal of covered stent 141 from a patient may be less difficult than the corresponding removal of uncovered stent 101.)

A sheath 151 coaxially surrounds much of the distal end of catheter 123 including stent 101. Sheath 151 is adapted for axial movement relative to catheter 123, and a handle 153 is disposed at the proximal end of sheath 151 for use in axially moving sheath 151 relative to catheter 123.

System 121 is used in much the same way as system 71 described above, stent 101 being deployed by (i) inserting the distal end of system 121 through the perforations in the stomach and pseudocyst previously created by needle 131, (ii) withdrawing sheath 151, (iii) expanding balloon section 135 and stent 101 until stent 101 reaches its desired diameter, (iv) deflating balloon section 135, and (v) withdrawing catheter 123.

One possible advantage of system 121 relative to system 71 is that balloon section 135 of system 121 may be capable of creating perforations of larger diameter in the pseudocyst and stomach than those capable of being created by self-expanding stent 11.

Figure 10:
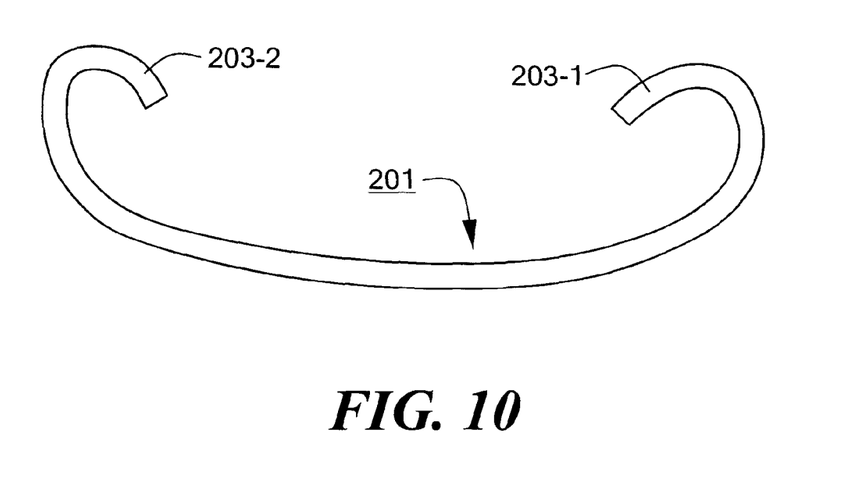
FIG. 10 is a side view of a sixth embodiment of a stent adapted for use in draining a gastric pseudocyst in accordance with the teachings of the present invention.

Referring now to FIG. 10, there is shown a sixth embodiment of a stent adapted for use in draining a gastric pseudocyst in accordance with the teachings of the present invention, said stent being represented generally by reference numeral 201.

Stent 201, which is commonly referred to in the art as a double pigtail stent, is a hollow member whose flexible ends 203-1 and 203-2 are curled in their relaxed states but are adapted to be straightened when a straightening force is applied thereto. Stent 201, which is preferably made of a flexible plastic, has a fixed diameter of about 10–11.5 Fr and a relaxed length of about 3–5 cm.

Figure 11A:
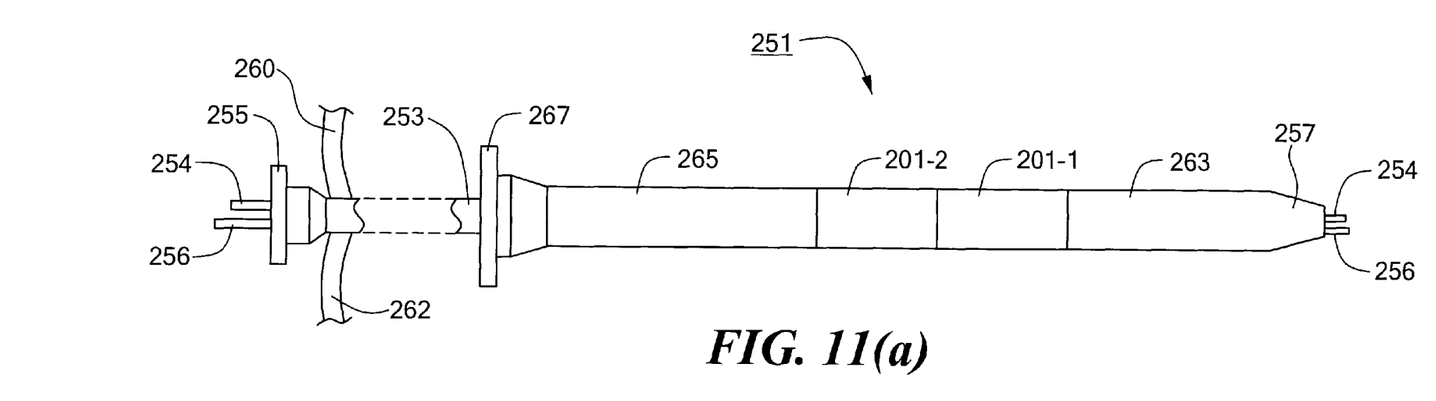
FIGS. 11(a) and (b) are fragmentary side and fragmentary schematic longitudinal section views, respectively, of a third embodiment of a stent delivery system constructed according to the teachings of the present invention, said stent delivery system including the stent of FIG. 10.
Figure 11B:
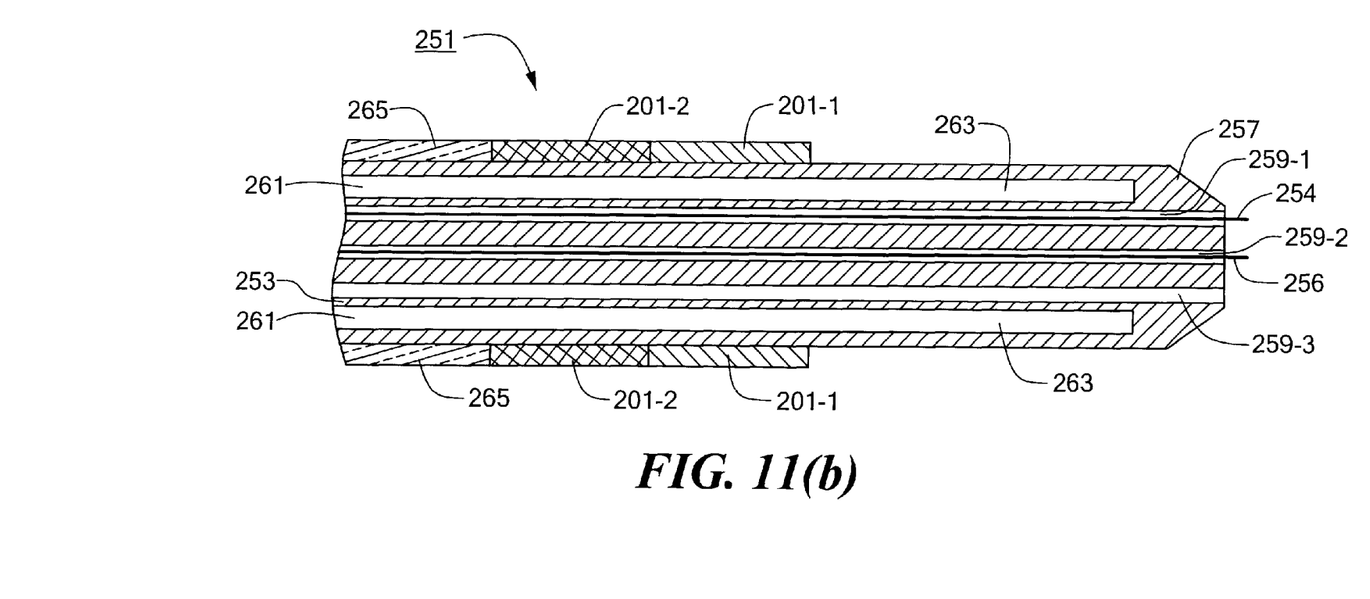

Referring now to FIGS. 11(a) and (b), there are shown fragmentary side and fragmentary schematic longitudinal section views of a third embodiment of a stent delivery system constructed according to the teachings of the present invention, said stent delivery system being represented generally by reference numeral 251.

System 251 comprises a flexible catheter 253. A handle 255 is disposed at the proximal end of catheter 253, and a tip 257 is disposed at the distal end of catheter 253. A plurality of parallel lumens 259-1 through 259-3 extend longitudinally through the distal end of catheter 253. A guide wire 254 is removably received within lumen 259-1 and is adapted for use in positioning system 251 at a desired position within a body lumen. A retractable needle 256 (or retractable knife, sphincterotome or the like) is removably received within lumen 259-2 and is adapted for use in perforating the stomach and pseudocyst walls. (It should be noted that one of lumens 259-1 and 259-2 could be eliminated, with needle 256 removably inserted therein and then guide wire 254 removably inserted therein.) Lumen 259-3 is coupled at its proximal end to a line 260 containing a dye for use in performing a cystogram. A fourth lumen 261, which is connected at its proximal end to a gas line 262, surrounds the distal ends of lumens 259-1 through 259-3 and ends in a balloon section 263 proximal to tip 257.

System 251 also comprises a pair of double pigtail stents 201-1 and 201-2, said pigtail stents 201-1 and 201-2 being coaxially and slidably positioned over catheter 253 in an end-to-end arrangement proximal to balloon section 263. (Although in the present embodiment there are two stents 201, it can readily be appreciated that there could be as few as one such stent or as many as three or more such stents.)

A pusher sleeve 265 coaxially surrounds catheter 253 proximal to stents 201-1 and 201-2. Pusher 265, which is adapted for axial movement relative to catheter 253, has a handle 267 disposed at its proximal end for use in axially moving pusher 265 relative to catheter 253. Pusher 265 is adapted to engage the proximal end of stent 201-2 and to push stents 201-1 and 201-2 off the distal end of catheter 253.

In use, system 251 is first endoscopically introduced into the patient's stomach via the patient's mouth. Needle 256 is then used to perforate the stomach and the pseudocyst, respectively, and, thereafter, is retracted. Dye is transmitted through lumen 259-3, and a cystogram is performed to confirm entry into a pseudocyst. Assuming that entry into pseudocyst is confirmed, guide wire 254 is then inserted through the perforations, and balloon section 263 is passed over guide wire 254. Balloon section 263 is then expanded to dilate the aforementioned perforations and, thereafter, is deflated. Stents 201-1 and 201-2 are then sequentially pushed over the distal end of catheter 253 by pusher 265 for implantation across the perforations to fluidly inteconnect the stomach and pseudocyst.

It is to be understood that the various stents described above could also be used in the surgical approach described above to drain a pseudocyst to a point external to a patient's body, instead of draining the pseudocyst into the patient's stomach; however, such an approach would suffer from the above-described shortcomings typically associated with invasive surgery.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method of draining a pseudocyst present within a patient, said method comprising the steps of:

(a) providing a stent, said stent being transformable from a non-expanded state of comparatively lesser diameter to an expanded state of comparatively greater diameter, said stent having a first end and a second end;

(b) delivering said stent in said non-expanded state to a pseudocyst located within a patient;

(c) inserting said first end of said stent into the pseudocyst; and (d) transforming said stent from said non-expanded state to said expanded state;

(e) whereby the pseudocyst drains through said stent.

2. The method as claimed in claim 1 further comprising the step of inserting said second end of said stent into the stomach of the patient whereby the pseudocyst drains through said stent into the stomach.

3. The method as claimed in claim 1 wherein said stent is a self-expandable stent.

4. The method as claimed in claim 3 wherein said delivering step comprises maintaining said stent in said non-expanded state using a removable restraint and wherein said transforming step comprises removing said removable restraint from said stent to allow said stent to self-expand.

5. The method as claimed in claim 3 wherein said delivering step comprises mounting said stent on the distal end of a catheter in said non-expanded state using a removable restraint and then inserting the distal end of said catheter into a patient in the area of a pseudocyst.

6. The method as claimed in claim 3 wherein said stent is shaped to include a waist of comparatively lesser expanded diameter and a pair of cuffs on opposite ends of said waist of comparatively greater expanded diameter.

7. The method as claimed in claim 6 wherein said stent is made of a biocompatible nonabsorbable material.

8. The method as claimed in claim 6 wherein said stent is made of a biocompatible nonabsorbable polymeric material.

9. The method as claimed in claim 6 wherein said stent is made of a bioabsorbable material.

10. The method as claimed in claim 6 wherein said waist has an expanded diameter of about 8–10 mm, each of said cuffs has an expanded diameter of about 15 mm, and wherein each of said waist and said cuffs has a length of about 5–10 mm.

11. The method as claimed in claim 3 wherein said stent has a uniform expanded diameter.

12. The method as claimed in claim 3 wherein said stent is made of a braided filamentary material.

13. The method as claimed in claim 1 wherein said stent is a balloon-expandable stent.

14. The method as claimed in claim 13 wherein said delivering step comprises mounting said balloon-expandable stent, in said non-expanded state, over a deflated balloon catheter and then inserting said deflated balloon catheter into a patient in the area of a pseudocyst and wherein said transforming step comprises inflating said deflated balloon catheter until said balloon-expandable stent is transformed from said non-expanded state to said expanded state.

15. The method as claimed in claim 1 wherein said stent is a balloon-expandable covered stent.

16. The method as claimed in claim 15 wherein said delivering step comprises mounting said balloon-expandable covered stent, in said non-expanded state, over a deflated balloon catheter and then inserting said deflated balloon catheter into a patient in the area of a pseudocyst and wherein said transforming step comprises inflating said deflated balloon catheter until said balloon-expandable covered stent is transformed from said non-expanded state to said expanded state.

17. The method as claimed in claim 1 wherein said stent is nonabsorbable, said method further comprising the step of endoscopically removing said stent with a snare after drainage of the pseudocyst is complete.

18. The method as claimed in claim 1 wherein said delivering step is performed intraorally.

19. The method as claimed in claim 1 wherein said stent is a self-expandable stent, said stent being a one-piece member shaped to include a pair of end cuffs of comparatively large relaxed diameter and an intermediate section of comparatively small relaxed diameter.

20. The method as claimed in claim 1 wherein said stent is made of a bioabsorbable material.

21. The method as claimed in claim 1 further comprising, prior to said first end inserting step, forming a perforation in the pseudocyst and wherein said inserting step comprises inserting said first end of said stent through said perforation in the pseudocyst.

22. A method of draining a pseudocyst present within a patient, said method comprising the steps of:
(a) providing a stent, said stent being transformable from a non-expanded state of comparatively lesser diameter to an expanded state of comparatively greater diameter, said stent having a first end and a second end;
(b) delivering said stent in said non-expanded state to a pseudocyst located within a patient;
(c) forming a perforation in each of the pseudocyst and the stomach;
(d) then, inserting said first end of said stent through said perforations in the pseudocyst and the stomach and into the pseudocyst;
(e) inserting said second end of said stent into the stomach of the patient; and
(f) transforming said stent from said non-expanded state to said expanded state;
(g) whereby the pseudocyst drains through said stent into the stomach.

23. A method of draining a pseudocyst present within a patient, said method comprising the steps of:
(a) providing a stent, said stent being a self-expandable stent transformable from a non-expanded state of comparatively lesser diameter to an expanded state of comparatively greater diameter, said stent having a first end and a second end;
(b) delivering said stent in said non-expanded state to a pseudocyst located within a patient, wherein said delivering step comprises mounting said stent on the distal end of a catheter in said non-expanded state using a removable restraint and then inserting the distal end of said catheter into a patient in the area of a pseudocyst, wherein said catheter inserting step is performed intraorally using an endoscope;
(c) inserting said first end of said stent into the pseudocyst; and
(d) transforming said stent from said non-expanded state to said expanded state;
(e) whereby the pseudocyst drains through said stent.

24. A method of draining a pseudocyst present within a patient, said method comprising the steps of:
(a) providing a double pigtail stent, said double pigtail stent having a first end and a second end, each of said first and second ends being transformable from a straightened state, when constrained, to a curled state, when relaxed;
(b) coaxially mounting said double pigtail stent over the distal end of a catheter, whereby each of said first and second ends is in said straightened state;
(c) endoscopically introducing said double pigtail stent and the distal end of said catheter through the mouth and into the stomach of a patient in the vicinity of a pseudocyst;
(d) sliding said first end of said double pigtail stent off the distal end of said catheter, through the stomach and into the pseudocyst, whereby said first end is transformed from said straightened state to said curled state; and
(e) sliding said second end of said double pigtail stent off the distal end of said catheter into the stomach, whereby said second end is transformed from said straightened state to said curled state;
(f) whereby the pseudocyst drains through said stent into the stomach.

25. The method as claimed in claim 24 further comprising, after said endoscopic introducing step and before said sliding steps, the step of forming a perforation in each of the stomach and the pseudocyst and wherein said first end sliding step comprises sliding said first end of said double pigtail stent off the distal end of said catheter and through the perforations in the stomach and pseudocyst, respectively.

26. The method as claimed in claim 25 wherein the distal end of said catheter includes a balloon, said method further comprising, after said perforation forming step and before said sliding steps, the steps of inserting said balloon into said perforations, then inflating said balloon, then deflating said balloon and withdrawing said balloon from said perforations.

27. The method as claimed in claim 24 further comprising the step of endoscopically removing said double pigtail stent with a snare after drainage of the pseudocyst is complete.

* * * * *